(12) United States Patent
Panchbhavi (10) Patent No.: US 8,388,627 B2
(45) Date of Patent: Mar. 5, 2013

(54) SURGICAL LASER GUIDE AND METHOD OF USE

(75) Inventor: Vinod K. Panchbhavi, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1304 days.

(21) Appl. No.: 11/521,258

(22) Filed: Sep. 13, 2006

(65) Prior Publication Data

US 2007/0073296 A1 Mar. 29, 2007

Related U.S. Application Data

(60) Provisional application No. 60/716,810, filed on Sep. 13, 2005.

(51) Int. Cl.
*A61B 17/90* (2006.01)
*A61B 17/00* (2006.01)
(52) U.S. Cl. ............ 606/102; 606/86 R; 33/511; 33/512
(58) Field of Classification Search .................... 606/87, 606/88, 89, 96, 98, 102, 104; 600/141; 473/212, 473/220; 33/227, 281, 286, 290, DIG. 21, 33/512
See application file for complete search history.

(56) References Cited

U.S. PATENT DOCUMENTS

| | | | |
|---|---|---|---|
| 4,348,141 A * | 9/1982 | Dahl | 411/389 |
| 4,817,588 A * | 4/1989 | Bledsoe | 602/16 |
| 4,988,192 A * | 1/1991 | Knittel | 356/138 |
| 5,031,203 A | 7/1991 | Trecha | |
| 5,141,512 A * | 8/1992 | Farmer et al. | 606/87 |
| 5,191,411 A * | 3/1993 | Muckerheide | 348/61 |
| 5,207,429 A * | 5/1993 | Walmsley et al. | 473/220 |
| 5,367,779 A * | 11/1994 | Lee | 33/290 |
| 5,606,590 A * | 2/1997 | Petersen et al. | 378/177 |
| 5,810,750 A * | 9/1998 | Buser | 602/13 |
| 5,983,510 A * | 11/1999 | Wu et al. | 33/227 |
| 6,450,893 B1 * | 9/2002 | Primiano et al. | 473/220 |
| 6,605,005 B1 * | 8/2003 | Lin | 473/220 |
| 6,743,235 B2 * | 6/2004 | Subba Rao | 606/91 |
| 6,855,152 B2 | 2/2005 | Suhm et al. | |
| 7,306,525 B2 * | 12/2007 | Sawada | 473/212 |
| 7,335,167 B1 * | 2/2008 | Mummy | 600/587 |

* cited by examiner

*Primary Examiner* — Kevin T Truong
*Assistant Examiner* — Christian Sevilla
(74) *Attorney, Agent, or Firm* — Wong, Cabello, Lutsch, Rutherford & Brucculeri, LLP (57) ABSTRACT

Methods and apparatus for aligning two or more longitudinally space parts of a body, such as leg bones, prior to and/or during a surgical procedure using a laser light guide assembly are described. The apparatus may have a saddle for attachment to a specific body part, and comprises a first horizontally rotatable structural member pivotably secured to the saddle or other support means, and a second rotatable structural member aligned vertically and perpendicular to the first structural member. A laser light guide which includes a laser is attached to the second structural member, the laser capable of generating a laser light beam of sufficient strength and intensity to allow for alignment of the body parts prior to and during a surgical procedure.

9 Claims, 12 Drawing Sheets

SURGICAL LASER GUIDE AND METHOD OF USE

CROSS REFERENCE TO RELATED APPLICATIONS

The present application claims priority to U.S. Provisional Patent Application Ser. No. 60/716,810 filed Sep. 13, 2005, the contents of all of which are incorporated herein by reference.

FIELD OF THE INVENTION

The invention relates to alignment systems which provide a line on a surface as a positioning reference. More specifically, surgical laser guide systems are provided which mark a reference point on a reference surface with a beam projected by a laser or laser light emitting means. Particularly, laser alignment systems for use in aligning fractured long bones in a mammalian body are disclosed.

DESCRIPTION OF RELATED ART

The precise localization of position has always been critical to surgical operations, perhaps none as important as those operations involving the setting, aligning and positioning of fractured bones and more particularly, fractured long bones. Fractures in long bones are currently stabilized using a variety of internal or external fixation methods. However, restoring the correct anatomic alignment of the fracture(s) during these stabilization procedures can be challenging, especially if the fracture involves many fragments or has a complex pattern.

Among the most common of the long bone fractures are fractures of the tibial diaphysis. Displaced and unstable fractures are commonly treated with intramedullary nail fixation procedures [see, Winquist, R. A., et al., *J. Bone Joint Surg. [Am]*, 66: pp. 529-539 (1984); Brumback, R. J., et al., *J. Bone Joint Surg. [Am]*, 70: pp. 1453-1462 (1988)], as numerous studies have suggested that these procedures provie superior functional results, and lower complication rates compared to those obtained using other fracture treatment methods such as open reduction and internal fixation (ORIF), external fixation, unreamed nailing procedures, or cast immobilization. Despite the positive results obtained using such bone setting techniques as intramedullary nail fixation, a potentially serious but often under-appreciated or under-addressed complication of this and related procedures is rotational malreduction or rotational malalignment [Ricci, W. M., et al., *J. Orthopaedic Trauma*, 15: pp. 90-95 (2001)]. In addition to the cosmetic problems this can cause, torsional deformities leading to lower extremity arthrosis and other functional complications can arise, which in turn lead to corrective osteotomy and result in orthopaedic malpractice claims.

Malrotation following intramedullary nailing is sparsely reported in the literature, but has been reported to have an incidence varying from 0% to 6% in some studies up to an incidence range from 15% to 20% [Blachut, P. A., et al., *J. Bone Joint Surg. Am.*, 79: pp. 640-646 (1997); Puloski, S., et al., *J. Orthop. Trauma*, 18: pp. 397-402 (2004)]. In fact, high-energy, greater pre-reduction displacement and distal third fractures appear to be especially predisposed to rotational malreduction. Extra care during intraoperative reduction is often required in the treatment of these injury patterns in order to prevent or minimize malrotation or misalignment. However, this is not always sufficient, and there is a need to develop methods of assessing and maintaining intraoperative rotational reduction in order to limit post-fracture sequelae in patients suffering this and other related-types of injuries.

During the intramedullary nailing of a tibial fracture, for example, intra operative fluoroscopy or radiographs are often used to assess the alignment in different planes, such as assessing tibial torsion as a rotation of the proximal versus the distal articular axis in the transverse plane [Kahn, K. M. and Beals, R. K., *J. Trauma*, 53: pp. 549-552 (2002)]. Restoration of alignment in antero-posterior and lateral planes is by far easier to assess, using radiographic techniques. Rotational alignment at the fracture site itself can be assessed using radiographs obtained intra operatively if the fracture pattern lends itself to such assessment, i.e., if there are easily identifiable bony spikes or notches in a fracture pattern that is not very comminuted. In such instances, the reduction of the corresponding notches or spikes between main distal and proximal fracture fragments can translate into restoration of alignment in all planes including the rotational plane.

Often, however, there are situations where there is significant comminution at the fracture site and rotational alignment cannot be assessed at the facture site using standard radiographic techniques, or radiographic techniques alone. The currently practiced intra-operative method in these situations is to rely upon a clinical assessment by "eye-balling" the alignment. The tibial tuberosity in the leg aligns with the second digit in the foot, which can serve as a guide for "eye-balling" methods intra-operatively to restore and/or maintain rotational alignment in the leg with a tibial fracture.

The problem with such manual, "eye-balling" techniques lies in the fact that such techniques are subject to human error. In the common operation of intramedullary nailing of a tibial fracture using a knee support, the patella is moved over to one side by the nail-entry instrumentation assembly which is near the tibial tuberosity and this can distort the view. Such a distorted view can thus interfere with the accurate visual alignment of the tibial tuberosity with the second digit of the foot. Consequently, this currently used method in stabilizing tibial fractures lacks the accuracy and reliability necessitated to avoid the high incidence of tibial malrotations reported in the literature [Mazurek, M. T., Bosse, M. J., *Techniques in Orthopaedics*, 16: pp. 381-386 (2001); Kahn, K. M. and Beals, R. K., ibid.].

While these problems continue to exist, little work has been done to address the problems from a technological standpoint, with surgeons often opting to rely upon their surgical skills alone to provide satisfactory results. One attempt to address problems involving surgical navigation has been described in U.S. Pat. No. 6,855,152 to Suhm, et al. This patent offers a device to be used in combination with a surgical navigation system for defining the position of a straight line determined by an operating surgeon within a three-dimensional coordinate system in an operating theater. The three-dimensional coordinate system is described to be calculated from previously measured positions by a computer, which is also a part of the system. However, the complexity of this approach does not lend itself to easy adaptation by a large number of professionals. Further, this approach does not involve the use of laser emitting guides directly on a subject.

U.S. Pat. No. 5,031,203 to Trecha suggests a coaxial laser targeting device for use with X-ray equipment and surgical drill equipment during surgical procedures, such as setting long bone fractures by intramedullary nailing techniques. Disclosed therein is an X-ray machine having an X-ray gun portion for emitting X-ray radiation along a longitudinal axis and an X-ray collector portion spaced from the gun portion along the longitudinal axis for receiving the X-ray radiation, wherein a laser light emitting member is provided, disposed on the X-ray gun portion for emitting a beam of visible laser light. A target grid member is disposed on the X-ray collector portion for targeting the visible laser light in a coaxial relationship with the longitudinal axis of the X-ray radiation between the gun portion and the collector portion. One or more radiolucent laser light redirecting members are provided for adjustably redirecting the visible laser light from the laser light emitting member into coaxial alignment with the longitudinal axis of the X-ray radiation to give a visual indication of the central longitudinal axis of the x-ray radiation.

However, while useful, these techniques do not fully address the needs to prevent malrotation not only in fractures where intramedullary nailing is used, but more generally in any fractures involving long bones or a long portion of a body, necessitating a proper angular alignment of the bones in question. Thus, there exists a need for a simple, effective, and easy to use apparatus and method for determining and maintaining the correction rotational alignment of one or more bones in relationship to one another.

SUMMARY OF THE INVENTION

An object of the present invention is to provide a portable, economical, stable and easy to use apparatus for aiming and aligning a laser light on any part of a mammal's body selected by the user, so as to draw a line of alignment between the apparatus and the point on the body illuminated by the laser light.

The present disclosure provides a laser guide assembly for visually assessing the alignment of bones during surgical procedures is described, the assembly comprising a saddle, a first horizontally rotatable structural member pivotally secured to the saddle, a second structural member secured perpendicular to the first structural member, a laser emitting means secured to the second structural member, and an adjustment assembly for rotatably adjusting the laser emitting means both horizontally and vertically.

The disclosure also provides a method for projecting a reference line onto an part of a body so as to assess the alignment of bones during surgical procedures is described, wherein the method comprises contacting a laser guide assembly to a first surface of a mammal's body, adjusting the laser guide assembly relative to the first surface, and projecting a laser onto a second surface of the mammal's body to display the reference line.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION OF THE INVENTION

The present invention is directed to assemblies, means and methods to prevent or minimize rotational mal-alignment during or after surgical operations to repair fractures to one or more long bones within a mammal, particularly a human.

While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups. Further, as used herein, the term "mammal" refers to human beings, dogs, cats, horses, goats, sheep, cattle, pigs, and the like. Most preferably, the term "mammal" refers to human beings.

Figure 1:
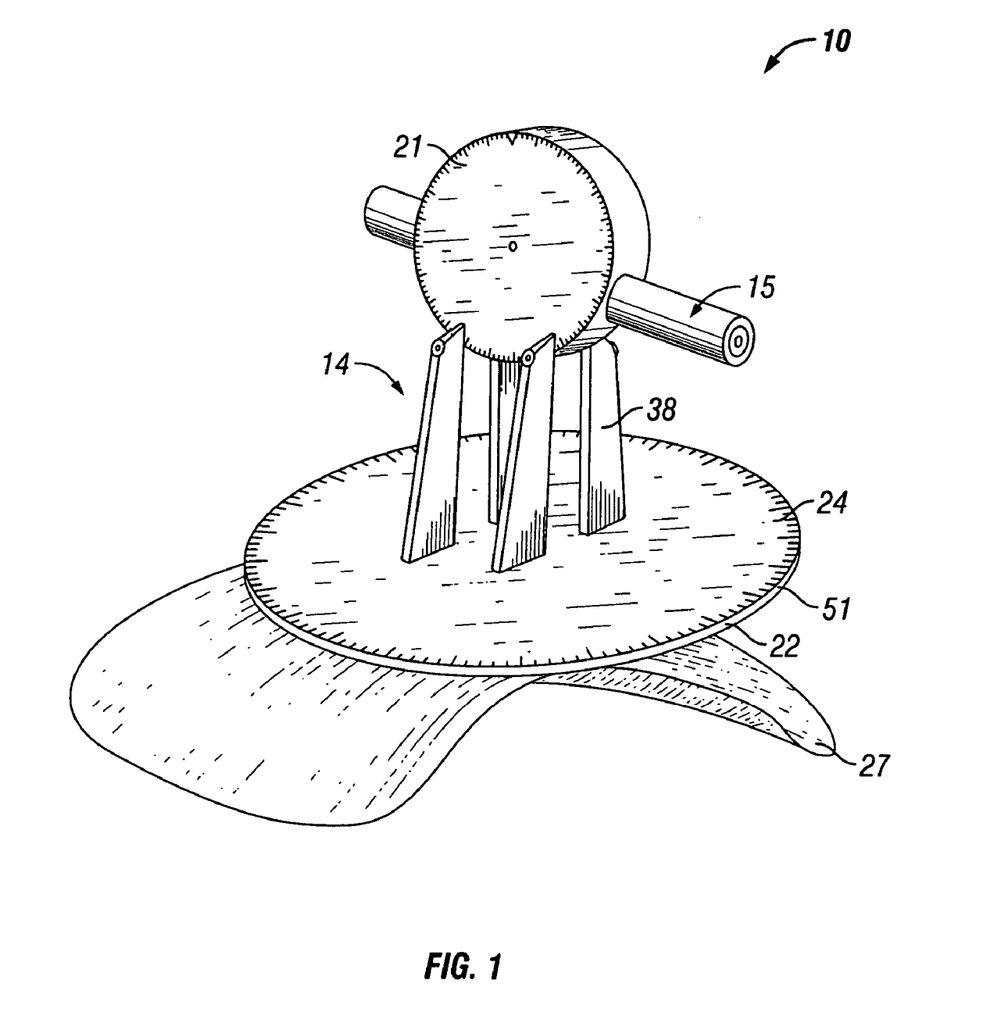
FIG. 1 illustrates a perspective view of a laser guide according to a further embodiment of the present invention.

A laser guide assembly 10 in accordance with a first aspect of the present invention is illustrated in FIG. 1, and comprises a laser light emitting assembly 15 or equivalent laser light emitting means and a laser light emitting assembly mount 14 which is perpendicularly attached to horizontal platform 24, which in turn is pivotally mounted to base 22 and saddle 27. Laser emitting means 15 is attached to altitude assembly 21 mounted on buttress supports 38.

The laser light emitting assembly mount 14 is an altitude-type mount and comprises a height assembly 20 and an altitude assembly 21 removably supported on the height assembly 20. A laser guide assembly 10 in accordance with certain aspects of the present disclosure is generally illustrated in FIGS. 1-6 and comprises a saddle 27, a base 22, a horizontal platform 24 and one or more vertical altitude bearing holders, such as the pair of vertical altitude bearing holders 26 illustrated, mounted on platform 24. Base 22 is preferably substantially planar and may optionally have feet (not shown) or similar assemblies for supporting the base in a substantially horizontal position on any suitable support surface, should saddle 27 be optionally omitted from the assembly system 10. Saddle 27 can be made of any number of suitable materials, both flexible and rigid, and can have various configurations and typically supports the base 22 in spaced relation to the support surface as shown in FIG. 1. In accordance with one aspect of the present disclosure, saddle 27 may be contoured and shaped so as to substantially follow the surface to which it is to be attached. Saddle 27 can be made of rubber or other suitable elastomeric materials, as well as silicone, plastics and polymers such as PVC, polystyrene, polybutadiene, polyacrylates, polymethacrylates, polyethylene, PET, and co-polymers and homopolymers thereof, as well as any number of other suitable materials which may be flexible or elastomeric, semi-rigid, or rigid as desired and as known to those of skill in the art. Attachment of saddle 27 can be by any number of appropriate means, which will often be governed by the anatomical area in which the system 10 is to be placed. Such attachment means can be adhesive attachment means, such as medical adhesives, tapes and glues, or can be more mechanical in nature, such as clamps, straps, surgical steel screw-type attachments, and the like, any of which are appropriate for attachment of saddle 27 to a surface. Additionally, and in accordance with one aspect of the present invention, the optional attachment or inclusion of saddle 27 in the assemblies described herein may be at a location intermediate between the surface of the anatomical region of the mammal to which it is to be attached (not shown) and base 22 or horizontal platform 24.

In accordance with further aspects of the present disclosure, saddle 27 may optionally contain one or more radio-opaque objects or radiographic markers 28 to aid in the placement of system 10. For example, radiographic markers 28 can be used to align, or assist the clinician/surgeon in the positioning of, the device of system 10 on a surface of a body, such as along a proximal bone, following which the alignment using the laser light emitting means 15 can be carried out as will be described in more herein. Alignment may be accomplished using any appropriate radio-opaque viewing assembly, system, program, or standard medical imaging equipment known and used in conjunction with the orthopedic or surgical arts. In accordance with this aspect of the present invention, suitable radio-opaque objects 28 which may be used in conjunction or combination with the surgical laser guide assembly described herein includes any of the variety of known radio-opaque objects and markers, having any appropriate shape, including spherical, discoidal, and the like. Additionally, radio-opaque objects 28 may be comprised of any number of suitable, radio-opaque materials, including chemicals and metals like zirconium and stainless steel, especially non-absorbable materials. Further, the radio-opaque objects 28 may be of any type, including but not limited to chemical- and periodic-element types (including both radioactive and non-radioactive markers, such as $^{123}$I, $^{67}$Ga, $^{111}$Im, and $^{99}$Tc), metabolic types, and mechanical types, such as self-drilling radiomarkers. As used herein, periodic-element type markers refer to markers that are a single element (radioactive or non-radioactive) or a combination of non-covalently-bonded elements of the Periodic Table of Elements, including but not limited to the transition elements, the Lanthanides, and the Actinides.

Platform 24 is mounted on base 22 for rotation relative to base 22 about a horizontal rotation axis 30 perpendicular to platform 24. The base 22 can be made of any suitable material and can have various peripheral configurations such as a circular peripheral configuration as shown for base 22. Base 22 is depicted as being of uniform thickness but may be of variable or non-uniform thickness. Platform 24 is planar and parallel to base 22 and can have any suitable peripheral configuration the same as or different from the peripheral configuration of the base 22. The platform 24 is depicted as having a circular peripheral configuration the same as the circular peripheral configuration of base 22. The peripheral configurations of the base 22 and the platform 24 are depicted as being the same size but could be of different sizes. The platform 24 is of uniform thickness but could be of non-uniform or variable thickness. The platform 24 can be made of any suitable material and can be fabricated integrally, unitarily or monolithically as one part or may be fabricated of multiple parts or sections.

A lower surface of platform 24 comprises a bearing surface 32 which may be formed integrally, unitarily or monolithically with the platform or as a separate material applied to the platform. Accordingly, the platform 24 and the bearing surface 32 may be made of the same material or of different materials. One typical material for the bearing surface 32 is Formica, although other materials known to those of skill in the art can be used. The bearing surface 32 can comprise one continuous bearing surface or a plurality of separate bearing surfaces not connected to one another. The bearing surface 32 can cover the entire or less than the entire surface area of the lower surface of platform 24. The bearing surface 32 is depicted as a continuous bearing surface covering the entire lower surface of platform 24.

A low friction surface 34 is disposed along an upper surface of base 22 in contact with the bearing surface 32 of platform 24. The low friction surface 34 may comprise one continuous low friction surface or a plurality of separate low friction surfaces not connected to one another. The low friction surface 34 can cover the entire or less than the entire surface area of the upper surface of base 22. The low friction surface 34 may be formed integrally, unitarily or monolithically with the base 22 or as a separate material applied to the base 22. The base 22 and the low friction surface 34 can be made of the same material or of different materials. A preferred material for the low friction surface 34 is Teflon, and the low friction surface 34 may comprise one or more Teflon pads of suitable thickness. The bearing surface 32 and the low friction surface 34 may be made of the same material or different materials. Of course, the arrangement of bearing surface 32 and low friction surfaces 34 shown in FIGS. 2 and 4 could be reversed in that the bearing surface 32 can comprise a plurality of individual bearing surfaces not connected to one another and covering less than the entire surface area of the lower surface of platform 24 while the low friction surface 34 may comprise a single continuous low friction surface covering the entire upper surface of base 22.

A pivot element 35 connects the platform 24 to the base 22 while permitting rotation of the platform 24 relative to the base 22 about the horizontal rotation axis 30. The pivot element 35 can comprise a pivot pin axially aligned with the horizontal rotation axis 30, which is located at the centers of base 22 and platform 24, and typically also extends into the center of saddle 27. The pivot element 35 may extend entirely through the thicknesses of the base 22, the platform 24, and at least a portion of the saddle 27 in a direction perpendicular to the planes of the base 22 and the platform 24. The pivot element 35 can comprise any suitable pivot structure, other than or in addition to a pivot pin, capable of mounting platform 24 for rotation relative to base 22 in a plane of the platform perpendicular to the horizontal rotation axis 30. As explained further below, rotation of the platform 24 relative to the base 22 about the horizontal rotation axis 30 is effected in response to horizontal or lateral movement of the laser light assembly 10 to provide horizontal positioning for the laser light means 15 when a horizontal or lateral aiming or pushing force is applied thereto. Contact between the bearing surface 32 and the low friction surface 34 provides sufficient friction to maintain the platform 24 stationary relative to the base 22 when no aiming or pushing force is applied to the assembly 10, while presenting minimal frictional resistance to rotation of the platform 24 relative to the base 22 when an aiming or pushing force sufficient to overcome the frictional force is applied to the assembly 10.

The altitude bearing holders 26 extend vertically upwardly from platform 24 in a perpendicular direction. The bearing holders 26 are planar and are mounted on platform 24 in spaced parallel relation to one another, with the azimuth rotation axis 30 centrally located between the bearing holders 26. Each bearing holder 26 has a concavely curving upper surface 36 extending between forward and rearward outer ends of the bearing holder. The upper surfaces 36 define the arc of a circle that is concentric with the circle defined by convexly curving contact surfaces of a pair of altitude bearings of the altitude assembly 21 as explained further below. Each bearing holder 26 may be formed integrally, unitarily or monolithically as a single part or may be formed of multiple parts or sections.

Figure 3:
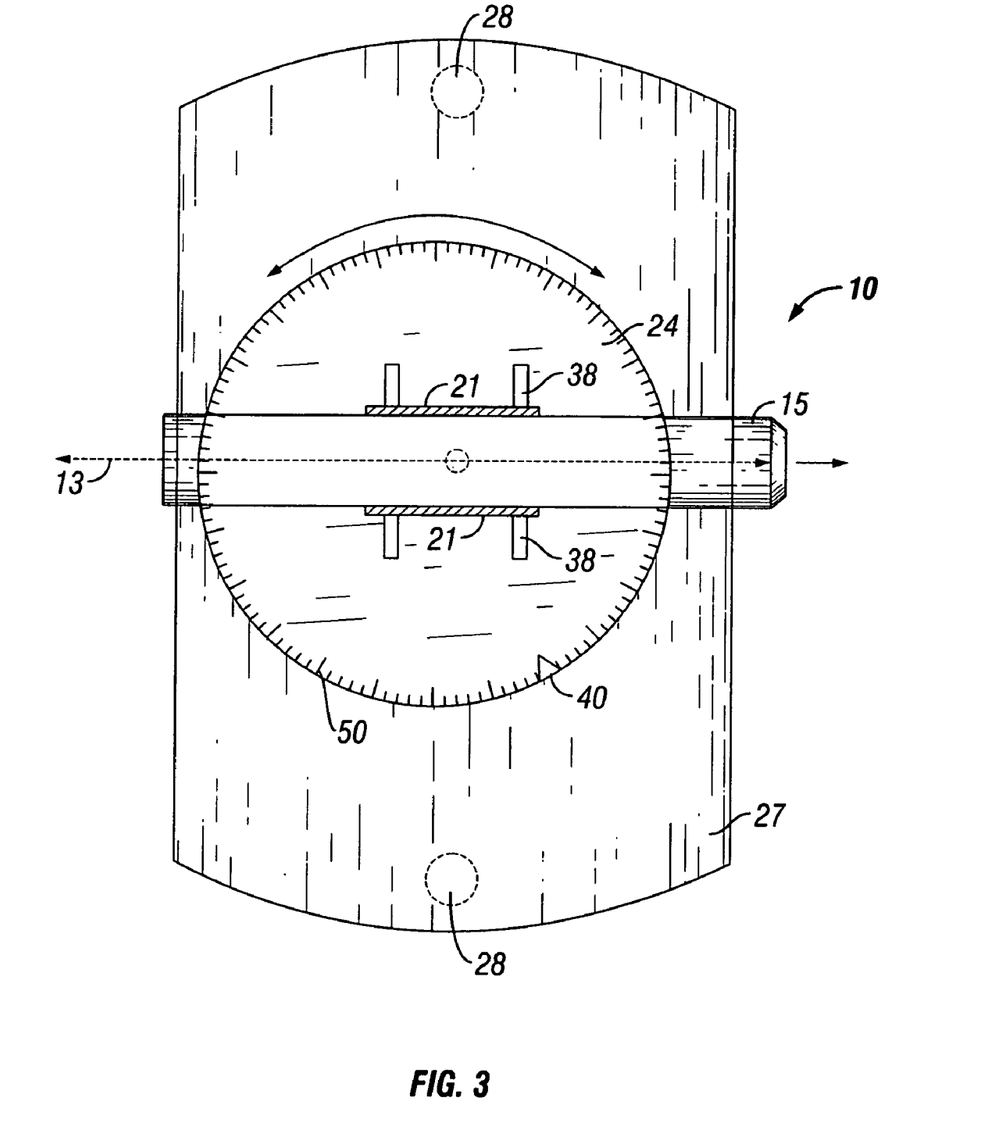
FIG. 3 illustrates a top view of the laser guide of FIG. 1.
Figure 4:
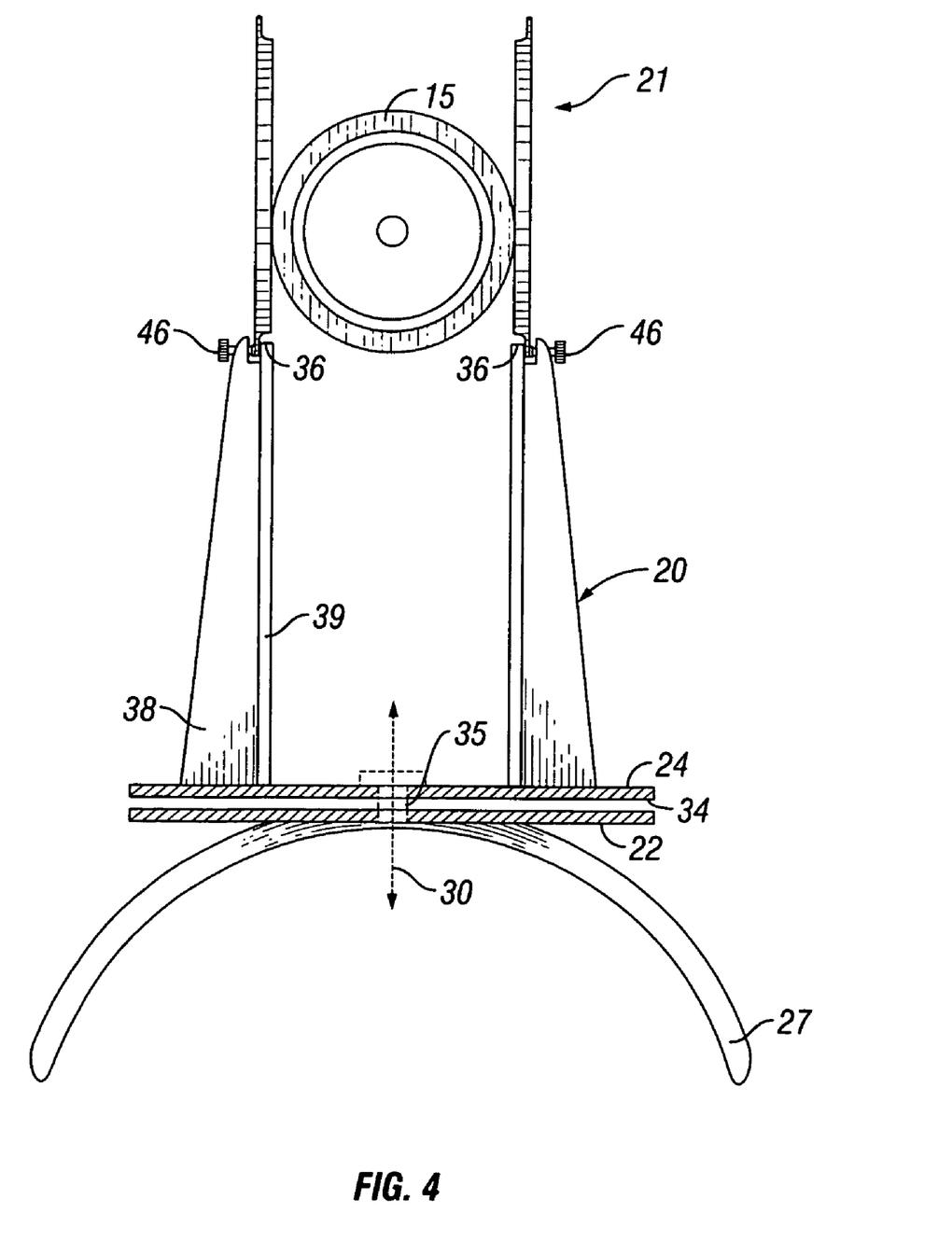
FIG. 4 illustrates an end view of the laser guide of FIG. 1.

The height assembly 20 can comprise various support structure for the bearing holders 26. The height assembly 20 includes one or more buttresses or flanges 38 and one or more wings 39 for each bearing holder 26. The buttresses 38 for each bearing holder 26 extend perpendicularly from the forward and rearward outer ends of the corresponding bearing holder 26 to the peripheral edge of the platform 24. Each buttress 38 of a bearing holder 26 can be contained in the same plane as a corresponding buttress 38 of the other bearing holder 26, and these planes are spaced from and parallel to one another. The buttresses 38 can also have a tapered configuration from bottom to top as seen in FIG. 3. The buttresses 38 can be planar, and can be of any uniform or non-uniform thickness. Each buttress 38 can be made integrally, unitarily or monolithically as a single part or may be made of multiple sections or parts.

The wings 39 for each bearing holder 26 extend from the forward and rearward outer ends of the bearing holder 26 to the peripheral edge of the platform 24 in a direction coplanar with the bearing holder 26. The wings 39 are planar and perpendicular to platform 24 and buttresses 38. The wings 39 preferably have a tapered configuration from bottom to top as seen in FIG. 1. The wings 39 may be of uniform or non-uniform thickness. Each wing 39 may be made integrally, unitarily or monolithically as a single part or may be made of multiple parts.

The wings 39 can be formed integrally, unitarily or monolithically with the corresponding bearing holder 26 and/or with the corresponding buttresses 38, or the wings 39 may be formed as separate components. The buttresses 38 can be formed integrally, unitarily or monolithically with the corresponding bearing holder 26 and/or the corresponding wings 39, or the buttresses 38 may be formed as separate components. Any of the bearing holders 26, buttresses 38 or wings 39 can be formed integrally, unitarily or monolithically with the platform 24 or separately from the platform.

Figure 2:
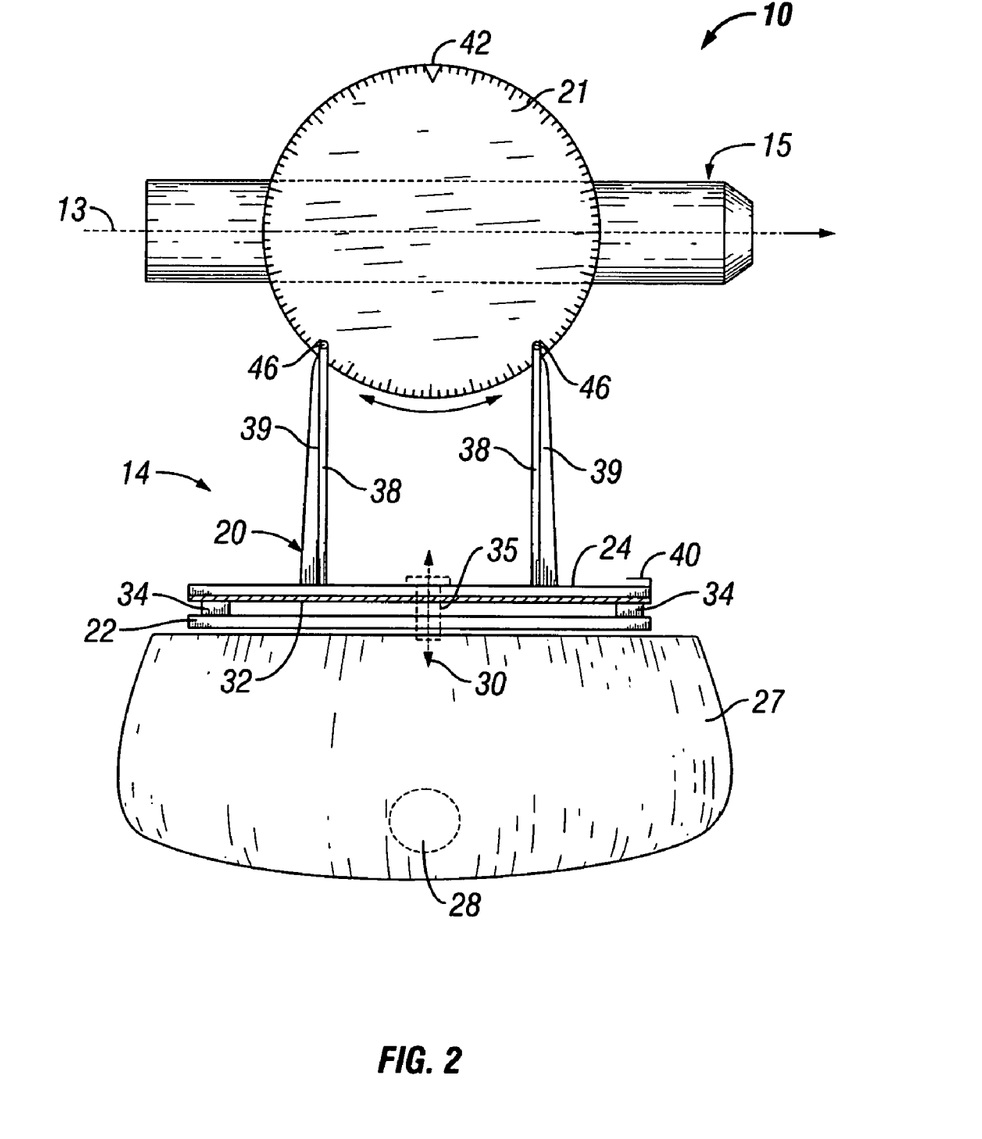
FIG. 2 illustrates a side view of the laser guide of FIG. 1.
Figure 5:
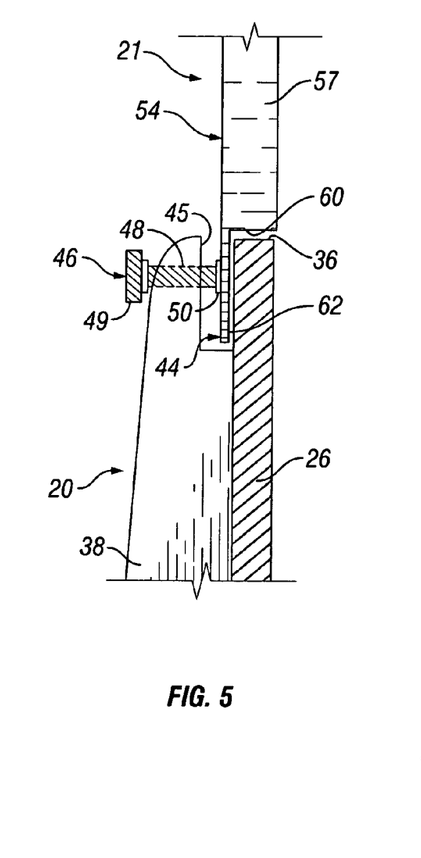
FIG. 5 illustrates an enlarged, detailed side view of the altitude mount of the laser guide of FIG. 1, particularly showing the frictional adjustment mechanism or lip lock.

Each upper surface 36 of bearing holders 26 has forward and rearward outer ends at which the upper surface 36 is disposed the greatest vertical, perpendicular distance (height) from the horizontal platform 24. The buttresses 38 have upper ends adjacent to the outer ends of the upper surfaces 36. As best shown in FIG. 5, a notch 44 can be formed in the upper ends of the buttress 38, each notch 44 being open at its top and closed at its bottom by a floor. Each notch 44 defines a slot between a shoulder 45 of the buttress 38 of vertical assembly 20 and an outer surface of the corresponding bearing holder 26 as illustrated in FIG. 5. A frictional adjustment mechanism or lip lock 46 is provided at the upper end of at least one buttress 38 and comprises a threaded extension element 48 extending through shoulder 45 perpendicular to the outer surface of the corresponding bearing holder 26. The extension element 48 has a knurled knob 49 at one end disposed along an outer surface of buttress 38 and a frictional end surface 50 at an opposite end disposed in the slot defined between shoulder 45 and bearing holder 26. The distance that the frictional end surface 50 extends from the shoulder 45 into the slot is screwably adjustable. The extension element 48 can comprise a screw threadedly engaged in a passage through the shoulder 45. The distance that the frictional end surface 50 extends from shoulder 45 into the slot is adjustable by turning or rotating the screw via the knob 49 to selectively extend and retract the screw relative to the shoulder 45. The frictional end surface 50 typically comprises a felt pad on the end of the extension element. However, the frictional end surface 50 could be formed integrally, unitarily or monolithically with the extension element or separately therefrom, and can be made of the same or different material as the extension element. The vertical assembly 20 includes at least one but may include more than one frictional adjustment mechanism 46 at the outer ends of the upper surfaces 36. FIG. 2 depicts a frictional adjustment mechanism 46 at the upper end of each buttress 38.

Figure 6:
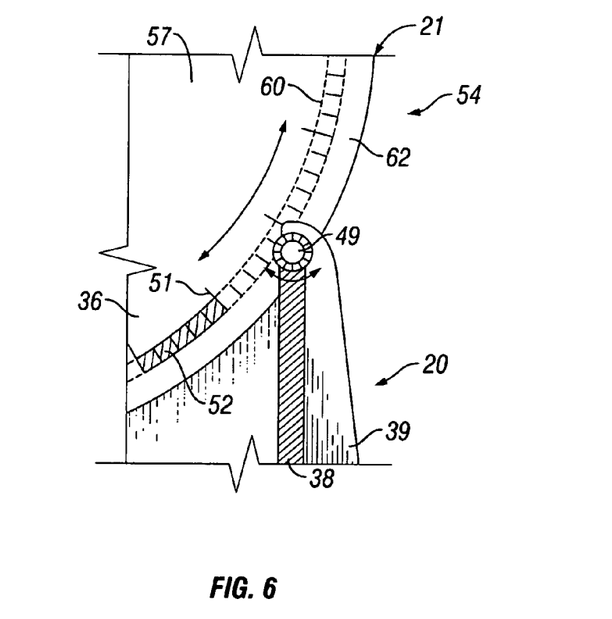
FIG. 6 illustrates an enlarged, detailed front view of an altitude mount for the laser guide of FIG. 1, showing a frictional adjustment mechanism or lip lock of the altitude mount.

In addition to degree graduations 51 along surface 36 of altitude assembly 21, a bearing surface 52 having low friction properties can be disposed along each upper surface 36 of the bearing holders 26 as illustrated in FIG. 6. Each bearing surface 52 can comprise a single continuous low friction bearing surface covering the entire or less than the entire upper surface 36 or can comprise a plurality of separate low friction bearing surfaces 52 not connected to one another and covering the entire or less than the entire upper surface 36. FIG. 6 depicts the bearing surface 52 as comprising a continuous low friction bearing surface 52 spaced along the outer periphery of upper surface 36. In the embodiment of FIG. 6, the low friction bearing surface 52 can be made of Teflon or comprise a plurality of Teflon pads. The number of and spacing for the individual bearing surfaces 52 along the upper surface 36 can vary. The low friction bearing surface 52 can be formed integrally, unitarily or monolithically with the corresponding bearing holder 26 or as a separate material disposed on the upper surface 36 of the bearing holder. The material used for bearing surface 52 can comprise any of various known, low friction materials which can be the same as or different from the material of the upper surface of the bearing holder. As illustrated in FIG. 6, the low friction bearing surface 52 follows the arcuate configuration of the upper surface 36 and can further define a concavely curved track, if desired. The "track" defined by the bearing surface 52 defines a circle that matches or is complementary to the circle defined by the convexly curving contact surfaces of the altitude bearings as explained further below.

The altitude assembly 21 can comprise a pair of vertical altitude tools 54 rigidly connected in parallel spaced relation and a clamp assembly 56 disposed between the altitude tools 54. The altitude tools 54 can each have a planar body 57 of generally circular configuration defining a circumferential contact surface 60, and a circumferential lip 62 extending outwardly from the planar body 57. The lip 62 is planar and has an outer surface coplanar with an outer surface of the planar body 57. The lip 62 can be of equal or of lesser thickness than the body 57 and has an inner surface spaced inwardly of an inner surface of the planar body 57, with the contact surface 60 extending from the inner surface of the body 57 to the inner surface of the lip 62. The contact surface 60 is convexly curving and defines a circle having a circumference complementary to or matching the circumference of the circle defined by the upper surface of low friction bearing surfaces 52 of upper surfaces 36. The lips 62 have circumferential peripheral edges, respectively, concentric with the contact surfaces 60. The bearings 54 may be made of any suitable material of sufficient rigidity and strength with contact surfaces 60, such as Teflon. The bearings 54 can be made in their entireties of the same material as the contact surfaces 60.

In one aspect of the present invention, the laser light emitting assembly or means 15 is shaped in the form of a body having a prismatic or cylindrical rod-type shape, provided with a longitudinal axis. However, it will be understood that this is in no means meant to be limiting, and assembly 15 and the corresponding body may be of any appropriate shape, such as rectangular, cylindrical, conical, and the like. Typically, the laser is integrated in the rod or body in such a way that the central beam coincides with the longitudinal axis of the rod and the emitted laser light beam is directed away from one of the rod ends. In a further aspect of the present invention, the laser light emitting assembly or means 15 may be realized in the form of a planar structure, including diode-type lasers that emit laser light in a planar manner. In accordance with this aspect, the emitted laser light beam is substantially planar as it is directed away from one of the planar ends of the assembly 15.

Regardless of the shape or size of the laser light emitting assembly or means 15 used in accordance with the present invention, the laser radiation generated is typically in the range from about 300 nm to about 700 nm, more preferably from about 600 nm to about 700 nm, with a wattage range from about 0.5 milliwatt (mW) to about 25 mW, and more preferably in a wattage range from about 1 mW to about 5 mW. Such laser light emitting means include helium-neon (HeNe) gas lasers generating laser radiation at about 633 nm, diode lasers generating beams in a range from about 630 nm to about 690 nm (including, for example, from about 635 nm to about 660 nm), and frequency-doubled Neodymium:YAG lasers with a blocked infrared component with wavelengths of about 533 nm (green emitted light). Typically, such laser light emitting means 15 suitable for use herein include Class 1, class 1M, class 2, class 2M, class 3A, class 3M, class 3B, or class 4 lasers, as classified according to the ANSI classification scheme (ANSI Z136.1-1993, American National Standard for Safe Use of Lasers). In accordance with one aspect of the present disclosure, the laser light emitting means 15 includes a class 2, class 2M, class 3A, or class 2M/3R type laser.

Figure 7:
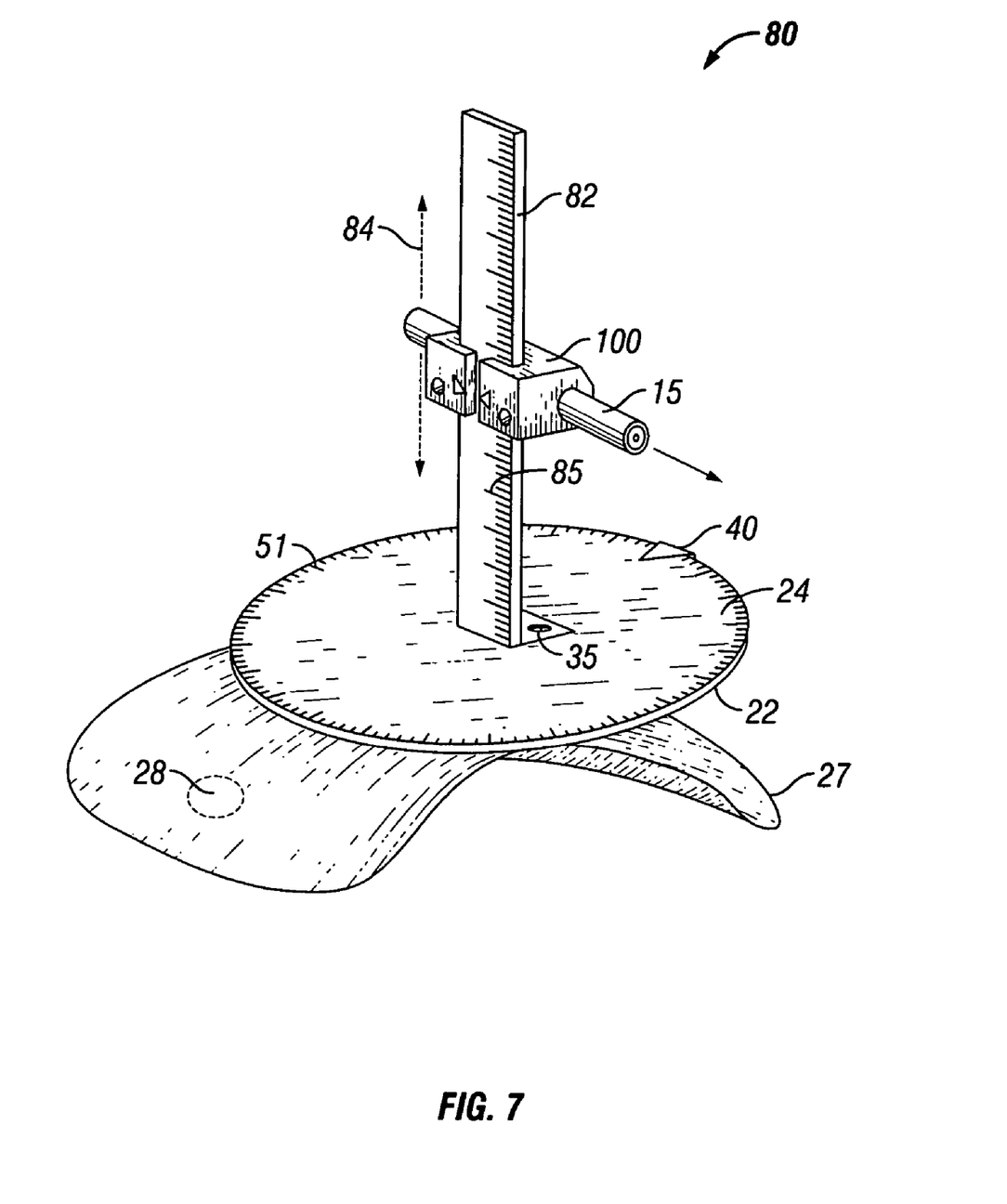
FIG. 7 illustrates a perspective view of a laser guide according to a first embodiment of the present invention.

Another feature of the present invention is illustrated in FIG. 7, wherein the laser guide assembly 80 comprises a saddle 27, a base 22 pivotably mounted to saddle 27, a horizontal platform 24, vertical alignment guide 82, and a laser emitting means 15 securably attached to a clamp holder 100 capable of vertical movement upward and downward along the vertical axis 84 of vertical means 82. Vertical alignment guide 82 can be rotatably mounted by pivot element 35 to the upper surface of horizontal platform 24 in a substantially perpendicular manner. As shown in FIG. 7, and as described previously, saddle 27 can contain one or more radiographic markers 28 for use in positioning assembly 80 over a portion of a mammalian body. Further horizontal platform 24 can have a plurality of graduations 51, such as degree graduations ranging from 0° to about 360°, for use in horizontal directional alignment of assembly 80. Optional pointer 40 can also be included in combination with horizontal platform 24 for use in selecting the degree which the assembly is horizontally rotated to. Vertical alignment guide 82 can also optionally have a plurality of graduations 85, which can be height increments (e.g., millimeters or centimeters) upward from the surface of platform 24. Such graduations can be permanently etched or built into vertical alignment means 82, or can be added after manufacture.

Figure 8:
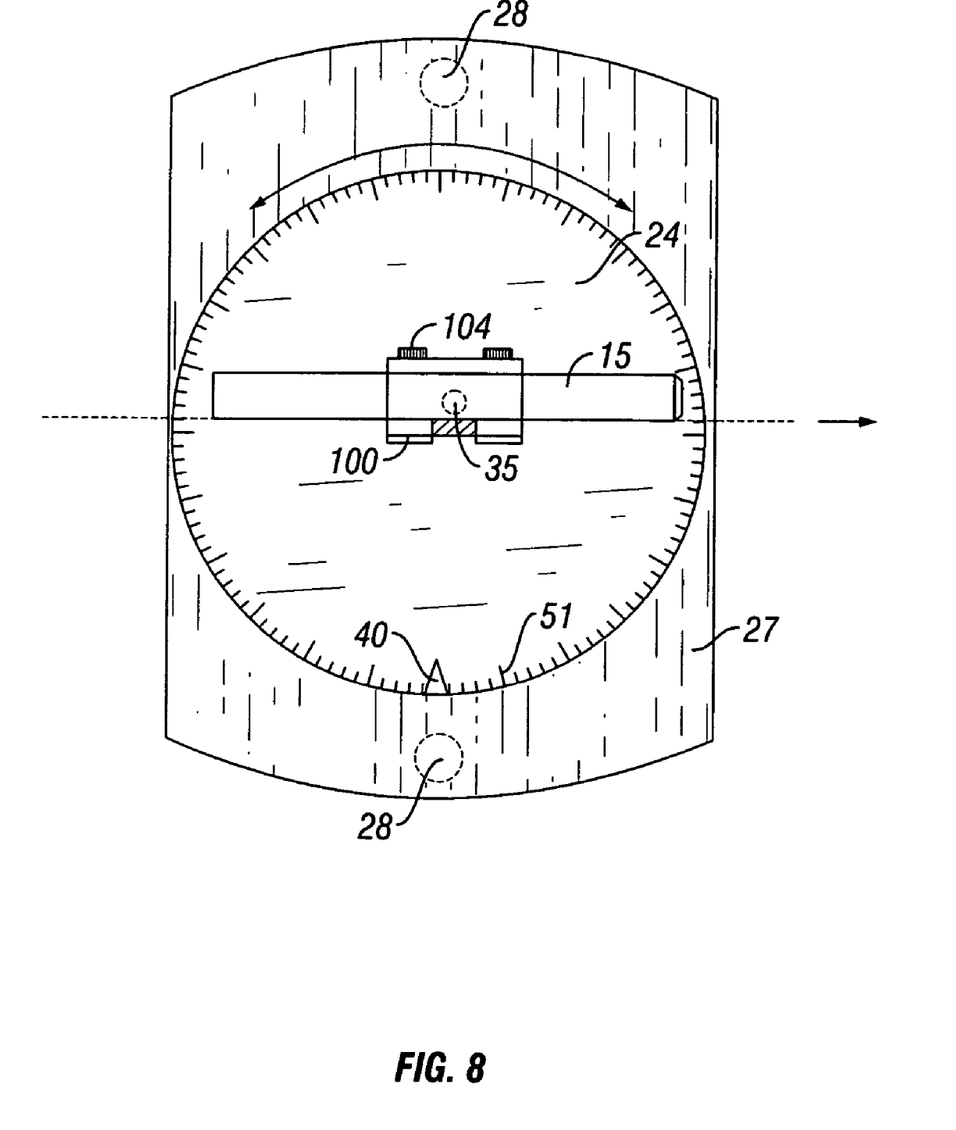
FIG. 8 illustrates a top view of the laser guide of FIG. 7.
Figure 9:
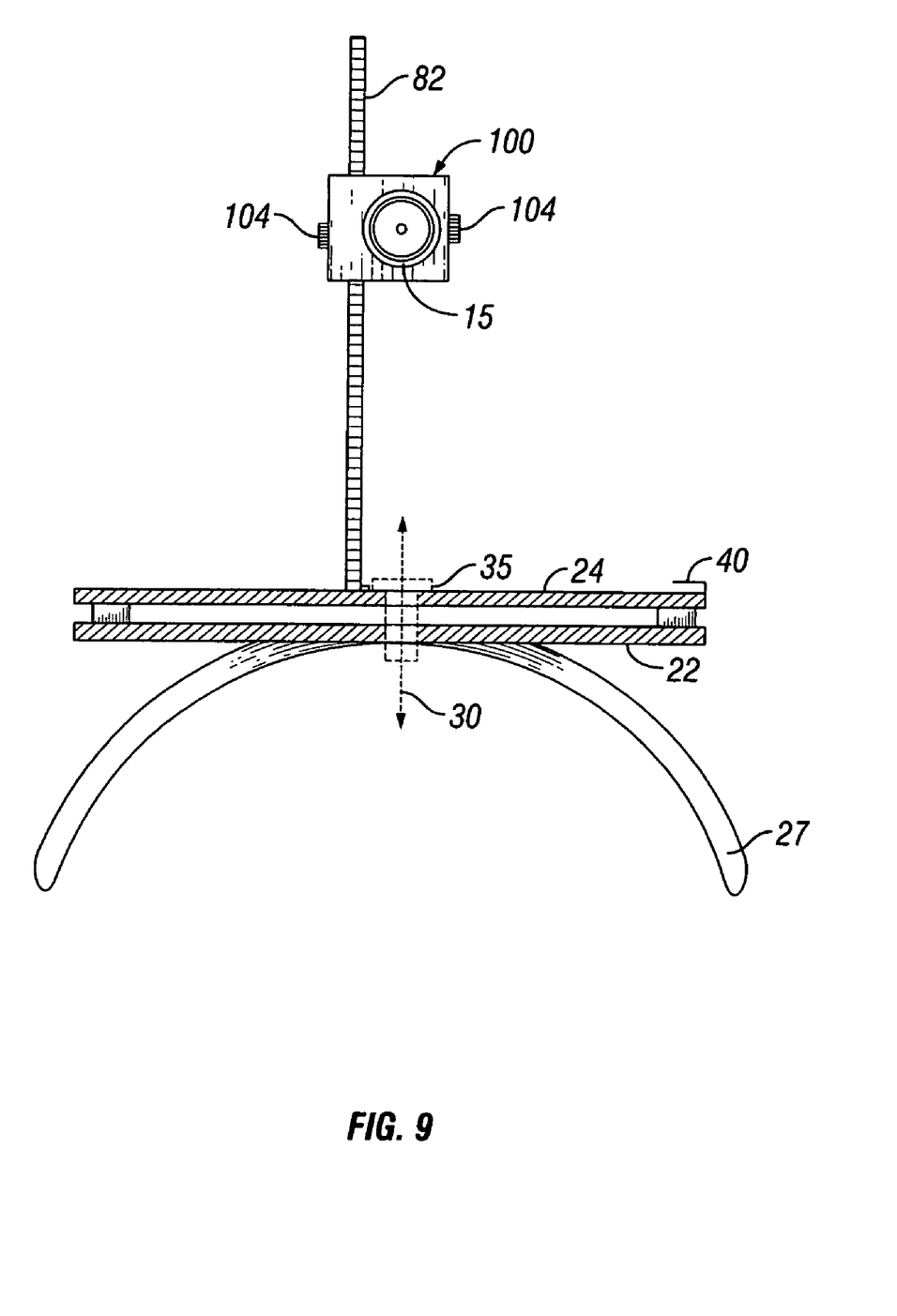
FIG. 9 illustrates an end view of the laser guide of FIG. 7.

FIGS. 8 and 9 illustrate the surgical laser guide assembly 80 of FIG. 7 in a top and side perspective, respectively. As illustrated in FIG. 8, the radiographic markers 28 located on or within saddle 27 can be oriented in a substantially parallel manner. Optionally, radiographic markers 28 can be oriented in any number of ways, depending upon how best to define the position over which saddle 27 is centered. FIG. 9 illustrates how pivot element 35 can connect horizontal platform 24 to base 22 and saddle 27 while permitting rotation of platform 24 relative to base 22 about the horizontal rotation axis 30. As described previously, pivot element 35 can comprise a pivot pin axially aligned with the horizontal rotation axis 30, which is typically located at the centers of base 22 and horizontal platform 24. The pivot element 35 preferably extends entirely through the thickness of platform 24, base 22, and saddle 27 in a direction perpendicular to the planes of the base 22 and the platform 24. The pivot element 35 can comprise any suitable pivot structure, capable of mounting platform 24 for rotation relative to base 22 and saddle 27.

Figure 10:
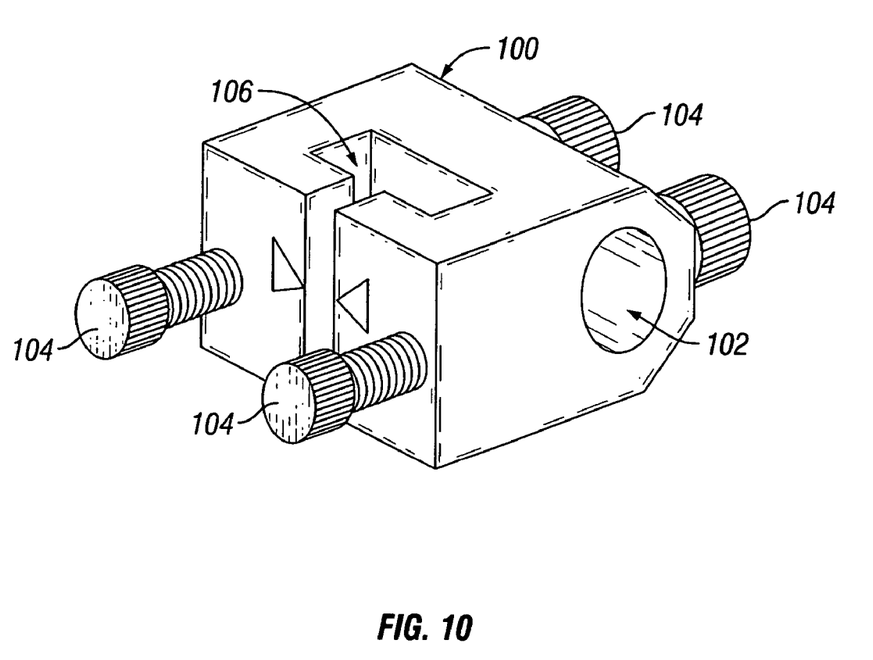
FIG. 10 illustrates a perspective view of a clamp for use in accordance with the laser guide of FIG. 7.

FIG. 10 shows a clamp holder 100 of the type suitable for use in accordance with the system shown in FIG. 7. The securing mechanisms 104 are embodied in threaded, locking or combination devices well known in the art. Preferred embodiments are threaded, machined devices having standard or metric threads and head design types that include, but are not limited to, slotted, philips, hex-head, allen-key, headless, socket, cap, tri-wing, button, jiglatch, spanner, notched spanner, torx, and thumb. Thumb types are further embodied in tee, knurled and rosette. Tips of the threaded devices are embodied in the following types, which include but are not limited to pointed, cup point, flat point, half dog point and hollow lock. All the tip types can be usefully employed with knurled ends. The most preferred embodiment is a standard threaded, knurled, allen-key socket cap screw with a flat point tip. The securing device can be manipulated by hand or mechanically using tools well known in the art.

The clamp body 100 can be manufactured from commercially available metal alloys known in the art to have sufficient mechanical strength, preferably metal alloys of aluminum, stainless steels and low carbon steels. Corrosion resistant alloys are preferred. The openings of the clamp are preferably machined into the body and may also be disposed at a range of angles from each other. Optionally, a plurality of mutually orthogonal openings can be machined into a clamp body or a plurality of openings having a plurality of angular or geometric relationships can be machined into a clamp body according to an embodiment of the invention.

The clamp body 100 for use with laser alignment systems of the present invention can be easily manufactured as a one-piece unit or in segments from commercially available metals and their alloys. Preferred metal alloys are Al (e.g. ASTM 6061), low carbon steels (e.g. ASTM 1018), stainless steels (e.g. ASTM T-316), surgical grade stainless steels, and their respective equivalents. Equivalent materials such as ceramic materials, ceramic composites, modified and/or reinforced plastics and engineering plastics are usefully employed in accordance with the invention. Any biological materials having the requisite mechanical strength or any materials developed from biotechnological processes can be usefully employed in accordance with the present invention. The openings in the clamp body that are fastened to supporting rods may be easily machined in a variety of configurations, such as V-shaped, slotted, cylindrical or grooved. In a preferred embodiment, the openings are grooved to conform to a cylindrically shaped support rod. Moreover, the openings in the clamp body may be machined such that they are easily disposed at a variety of angles to one another. In separate embodiments, they may be machined such that the openings may be disposed at angles ranging from about 30 degrees to about 180 degrees from each other, depending on the orientation required to support the laser light emitting means. In a preferred embodiment, the openings are such that they are mutually perpendicular to each other. The exact dimensions of the clamp holder are dictated by the particular application. At a minimum, each opening in the clamp body should have at least two holes which engage securing mechanisms to fasten the clamp body to the vertical adjustment means.

Figure 11:
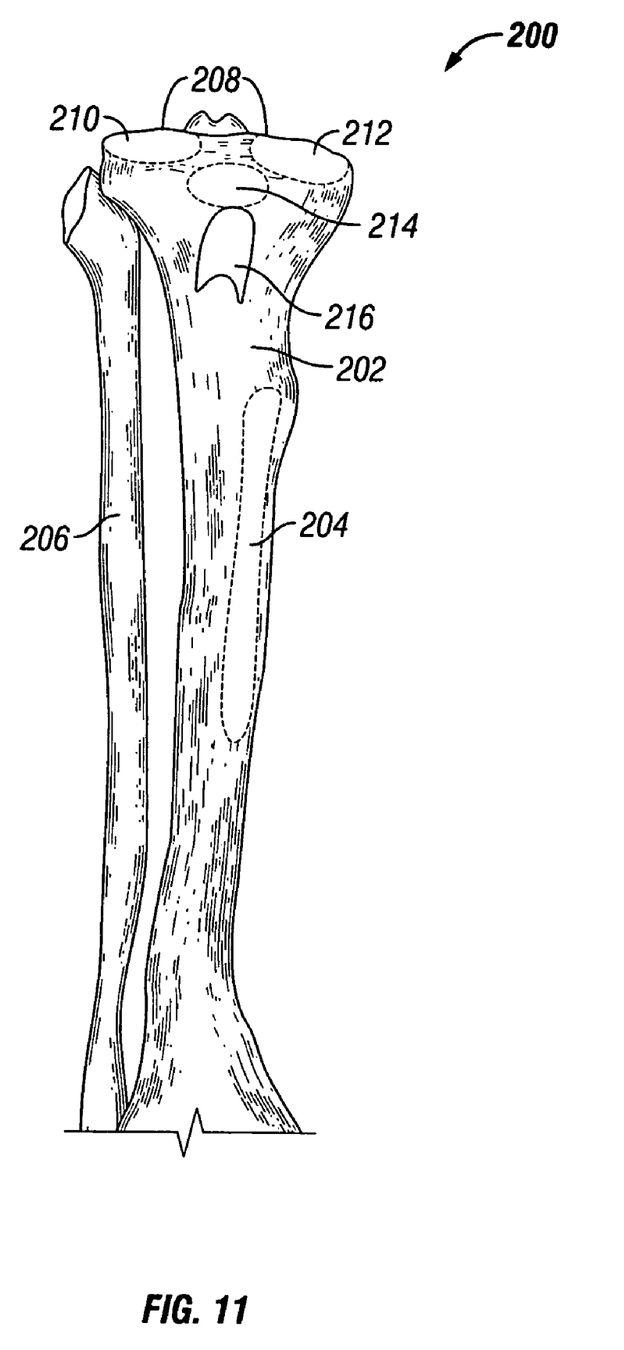
FIG. 11 illustrates a schematic of the tibia and fibula of a human leg.
Figure 12:
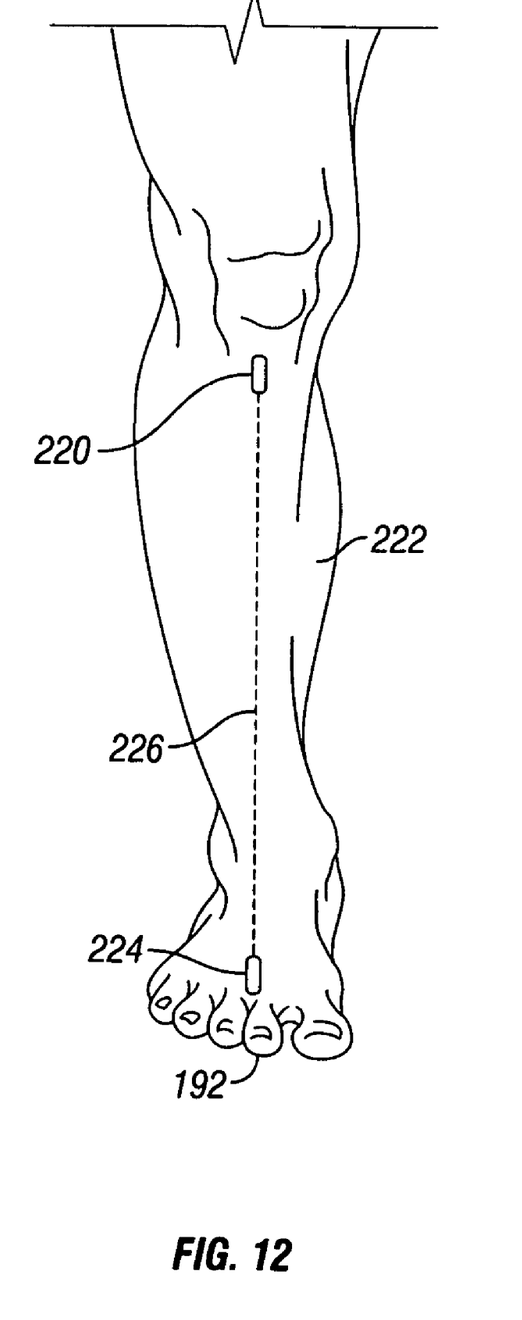
FIG. 12 illustrates a representation of the normal longitudinal axis of the tibia.

A general method of use of the systems of the present invention will now be described, using the alignment of the tibia in preparation for an intramedullary nailing as a general example. A general schematic of the bones of the lower leg are shown in FIG. 11, wherein right leg 200 is comprised of the tibia 202 and the fibula 206. Key points of reference for use within the scope of the present disclosure are the medial subcutaneous surface 204, the articular capsule 208, lateral condyle 210, medial condyle 212, the tibial tuberosity 214, and the ligament patellae, 216. These anatomical regions together form the basis for the representative longitudinal axis of the tibia shown in FIG. 12. As illustrated therein, the upper region of left leg 222 has a starting axis point 220, which is generally centered over the tibial tuberosity 214. A longitudinal axis line 226 can be drawn between point 220 and a second point 224 which is located just below the second digit 192 of the foot. In accordance with certain aspects of the present disclosure, point 224 is in the general region between the second and third phalanges of the foot, preferably just below the second phalange, or digit, 192 of the foot. Alignment of the leg, especially the tibia and fibula with regard to longitudinal axis line 226 allows for prevention of malrotation of the leg 222 during bone fracture repair in the leg of a patient.

Figure 13:
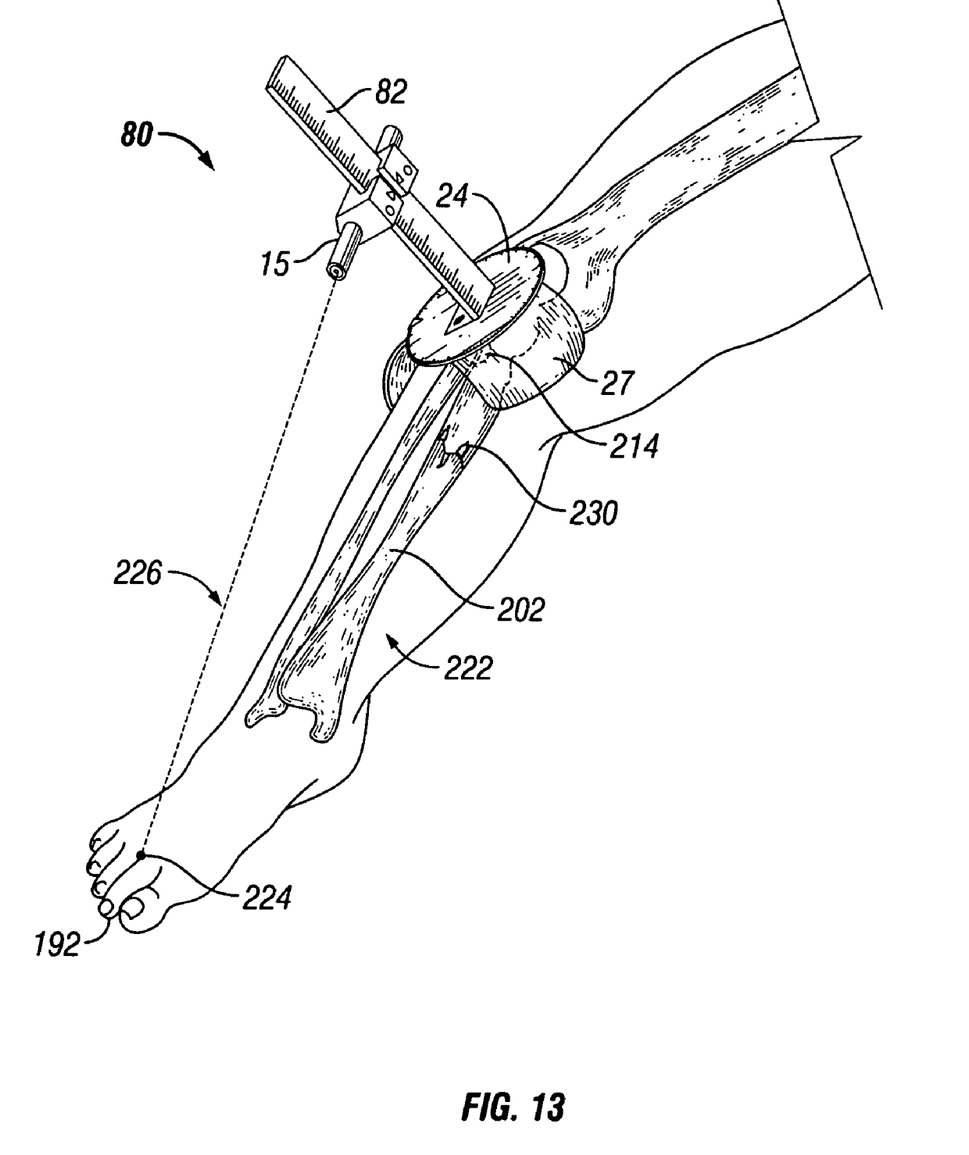
FIG. 13 illustrates a perspective view of a laser guide in accordance with the present invention in use during the repair of a lower leg fracture.

A general representation of a laser guide alignment system in accordance with the present invention is illustrated in FIG. 13. As depicted therein, an alignment system 80 in accordance with an aspect of the present invention is shown placed over the upper tibia region of leg 222, having a severe fracture 230 in tibia 202. Saddle 27 of system 80 is positioned and secured such that horizontal platform 24 is substantially centered over tibial tuberosity 214. Radiographic markers 28 (not shown, for clarity) are used to position alignment system 80 over tuberosity 214 by aligning with the lateral and medial condyles 210 and 212. Laser emitting means 15 is turned on, and horizontal platform 24 is then rotated as necessary to generally align laser 15 with the foot. Laser 15 can then be adjusted vertically as necessary along vertical alignment assembly 82, such that longitudinal axis line 226 defined by the light beam emitted by laser emitting means 15 is directed to point 224 just below second digit 192 of the foot. Horizontal and vertical alignment assemblies 24 and 82, respectively, can then be locked into place, and repair of fracture 230 using necessary surgical operations, e.g., intramedullary nailing techniques, can proceed with a reduced risk of mal-alignment occurring during the procedure.

While the present apparatus has been described herein for use in aiding in the repair of fractures to long bones in a mammalian body, such as the tibia or femur, it will be appreciated by those of skill in the art that the apparatus and methods of the present invention can be used to prevent rotational mal-alignment/malrotations of the femur in femoral shaft fractures, for example, as well as in the tibia and the fibula; to correct distal femoral nonunions and mal-alignments; in knee arthroplasty, such as for axial alignment using the transepicondylar and/or condylar line as parameters or references; in the alignment of the upper limbs, such as the humerus, radius, and ulna; and in the alignment of vertebrae during spinal alignment procedures. For example, it is envisaged that an apparatus such as described herein could be mounted at the base of the neck, i.e., between the first cervical vertebrae and the second cervical vertebrae. After centering and adjustment as warranted, the laser guide could be turned on, allowing a laser line of alignment to shine between the first cervical vertebrae and the fifth lumbar vertebrae.

The following example is included to demonstrate preferred embodiments of the invention. It should be appreciated by those of skill in the art that the techniques disclosed in the example which follows represents techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Use of Laser Guide in the Setting of a Tibial Fracture

A patient sustaining a twisting ground-level fall incurs a closed spiral fracture of the tibia and fibula at the junction of the middle and distal thirds of the shafts. The patient is positioned supine on a radiolucent table, and the leg flexed over a bump. A disposable, pre-packaged laser guide assembly in accordance with the present invention, having a base with a radiographic marker embedded therein, is removed from its sterile packaging and placed over the tibial crest, near the tibial tubercle prior to prepping and draping the patient. Using radiographs and the radiographic marker in the base of the assembly, the assembly is aligned over the tibial tuberosity and the laser emitting device is activated. The focus of the laser light emitted is adjusted to a focused point, and the focused point is then aligned with the second ray of the foot. Once aligned, the line of the laser light is longitudinally aligned with the longitudinal axis of the tibial tuberosity and the second ray of the foot. The patient is then treated with a reamed, statically locked intramedullary nail, during which process the rotational alignment of the tibia is marked and maintained in place by the laser light. In this manner, the correct alignment throughout the procedure is maintained, thereby lessening the chances for malrotation following the completion of the locked intramedullary tibial nailing procedure.

Additionally, the various methods and embodiments of the invention can be included in combination with each other to produce variations of the disclosed methods and embodiments, as would be understood by those with ordinary skill in the art, given the understanding provided herein. Also, various aspects of the embodiments could be used in conjunction with each other to accomplish the understood goals of the invention. Further, the directions such as "top," "bottom," "left," "right," "upper," "lower," and other directions and orientations are described herein for clarity in reference to the Figures and are not to be limiting of the actual device or system or use of the device or system. Unless the context requires otherwise, the word "comprise" or variations such as "comprises" or "comprising", should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. Further, the order of steps can occur in a variety of sequences unless otherwise specifically limited. The various steps described herein can be combined with other steps, interlineated with the stated steps, and/or split into multiple steps. The term "coupled," "coupling," "coupler," "attachment means", "attachment", and like terms are used broadly herein and can include any method or device for securing, binding, bonding, fastening, attaching, hingably attaching or joining, joining, inserting therein, forming thereon or therein, communicating, or otherwise associating, for example, mechanically, magnetically, electrically, chemically, directly or indirectly with intermediate elements, one or more pieces of members together and can further include without limitation integrally forming one functional member with another in a unity fashion. The coupling can occur in any direction, including rotationally. Additionally, the headings herein are for the convenience of the reader and are not intended to limit the scope of the invention All of the methods, processes and/or apparatus disclosed and claimed herein can be made and executed without undue experimentation in light of the present disclosure. While the methods, apparatus and processes of this invention have been described in terms of preferred embodiments, it will be apparent to those of skill in the art that variations may be applied to the methods, apparatus and/or processes and in the steps or in the sequence of steps of the methods described herein without departing from the concept and scope of the invention. For example, while objects of the present invention have been described as being in specific spatial relationships such as "parallel to" and "horizontal to", it is envisioned that such objects can also be at a variety of angles (e.g., acute, obtuse, or oblique angles) with respect to one another without departing from the scope of the present invention. More specifically, it will be apparent that certain features which are both mechanically and functionally related can be substituted for the features described herein while the same or similar results would be achieved. All such similar substitutes and modifications apparent to those skilled in the art are deemed to be within the scope and concept of the invention.

What is claimed is:

1. A method for fixation of a first bone fragment on a first side of a bone fracture and a second bone fragment on a second side of the bone fracture, comprising:
    contacting a concave interior surface of a laser guide assembly including a laser to a first surface of a mammal's body on the first side of the fracture;
    positioning the laser guide assembly relative to the first bone fragment;
    projecting a beam of the laser onto a second surface of the mammal's body on the second side of the fracture to produce a reference point;
    aligning the first bone fragment and the second bone fragment with regard to the reference point; and
    securing the first bone fragment to the second bone fragment such that the first bone fragment and the second bone fragment are in a position that is anatomically correct.

2. The method of claim 1, further comprising horizontally and/or vertically adjusting the laser within the laser guide assembly.

3. The method of claim 2, wherein horizontally adjusting the laser within the laser guide assembly comprises horizontally rotating a horizontal member within the laser guide assembly.

4. The method of claim 2, wherein vertically adjusting the laser within the laser guide assembly comprises vertically rotating the laser within the laser guide assembly.

5. The method of claim 2, wherein vertically adjusting the laser within the laser guide assembly comprises vertically sliding the laser within the laser guide assembly.

6. The method of claim 1, wherein the mammal is a human.

7. The method of claim 1, wherein positioning the laser guide assembly relative to the first bone fragment comprises detecting positioning of radio-opaque objects associated with the laser guide assembly relative to the first bone fragment.

8. The method of claim 1, wherein securing the first bone fragment to the second bone fragment comprises an intramedullary nailing.

9. The method of claim 1, wherein the bone fracture is in a leg bone.

* * * * *